United States Patent [19]

Aaserude et al.

[11] Patent Number: 4,699,129
[45] Date of Patent: Oct. 13, 1987

[54] POLYCENTRIC VARIABLE AXIS HINGE

[76] Inventors: Gordon V. Aaserude, 444 La Paloma, El Sobrante, Calif. 94803; Robert H. Rubin, 1033 Leneve Pl., El Cerrito, Calif. 94530

[21] Appl. No.: 904,562

[22] Filed: Sep. 5, 1986

[51] Int. Cl.$^4$ ............................................. A61F 5/01
[52] U.S. Cl. ..................................... 128/80 C; 128/77
[58] Field of Search .................. 403/53, 61, 116, 117, 403/55; 128/80 C, 88, 202.11, 77; 16/360, 361, 366, 337; 623/27, 39, 45

[56] References Cited

U.S. PATENT DOCUMENTS

| 58,403 | 10/1865 | Goodwin | 128/88 |
|---|---|---|---|
| 901,592 | 10/1908 | Clegg | 128/88 |
| 2,460,895 | 2/1949 | Meany | 128/80 C |
| 2,467,907 | 4/1949 | Peckham, I | 128/80 C |
| 2,632,440 | 3/1953 | Hauser et al. | 403/53 |
| 3,194,233 | 7/1965 | Peckham, II | 128/80 C |
| 3,528,412 | 9/1970 | McDavid | 128/89 R |
| 3,581,741 | 6/1971 | Rosman | 128/80 C |
| 3,779,654 | 12/1973 | Horue | 128/80 C |
| 3,902,482 | 9/1975 | Taylor | 128/88 |
| 4,219,892 | 9/1980 | Rigdon | 128/80 C |
| 4,249,524 | 2/1981 | Anderson | 128/88 |
| 4,323,059 | 4/1982 | Rambert et al. | 128/80 C |
| 4,337,764 | 7/1982 | Lerman | 403/116 |
| 4,340,041 | 7/1982 | Frank | 128/80 C |
| 4,409,689 | 10/1983 | Boring et al. | 128/80 C |
| 4,499,619 | 2/1985 | Kassai | 16/360 |
| 4,520,802 | 6/1985 | Mercer et al. | 128/80 C |
| 4,599,748 | 7/1986 | Gaucia | 128/80 C |
| 4,599,998 | 7/1986 | Castillo | 128/80 C |

FOREIGN PATENT DOCUMENTS 1011204 5/1977 Canada ............................ 128/80 C Primary Examiner—Richard J. Apley
Assistant Examiner—James Prizant
Attorney, Agent, or Firm—Harry A. Pacini

[57] ABSTRACT

A polycentric variable axis pivotal hinge system especially designed and adaptable to follow the complex movement of the knee when incorporated in orthotic devices, having an upper and a lower extension overlying a central linking member and pivotally connected thereto wherein each extension moves in a relative angular motion determined by the coaction of a guide pin follower slidably and pivotally interacting with slots in the angular terminal portions of the extensions and the guide pin follower moving in a vertical slot in the central member; with provision for motion limiting stops.

8 Claims, 4 Drawing Figures

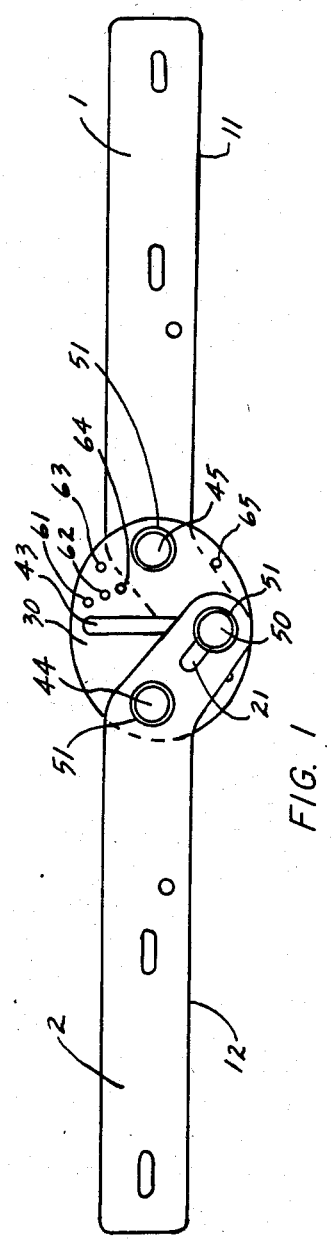
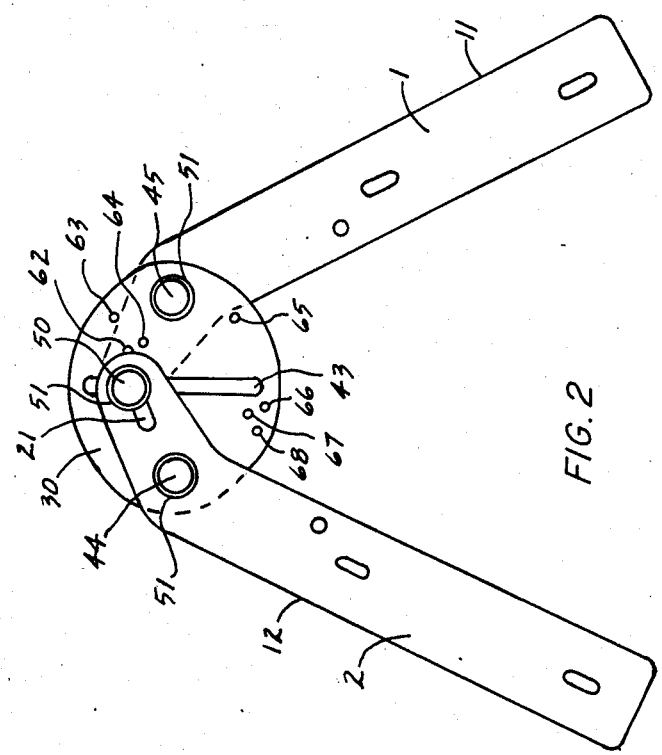

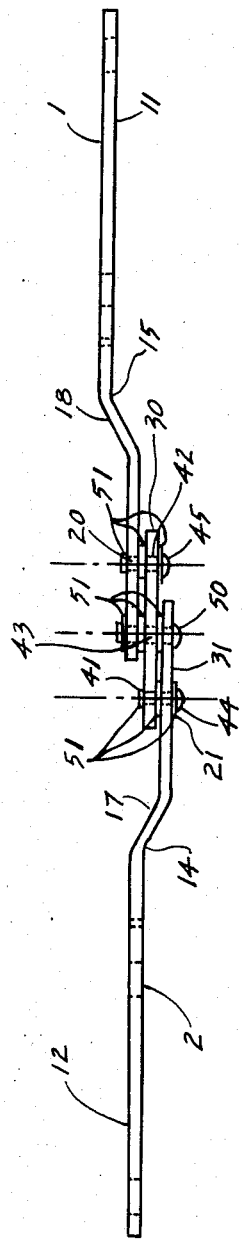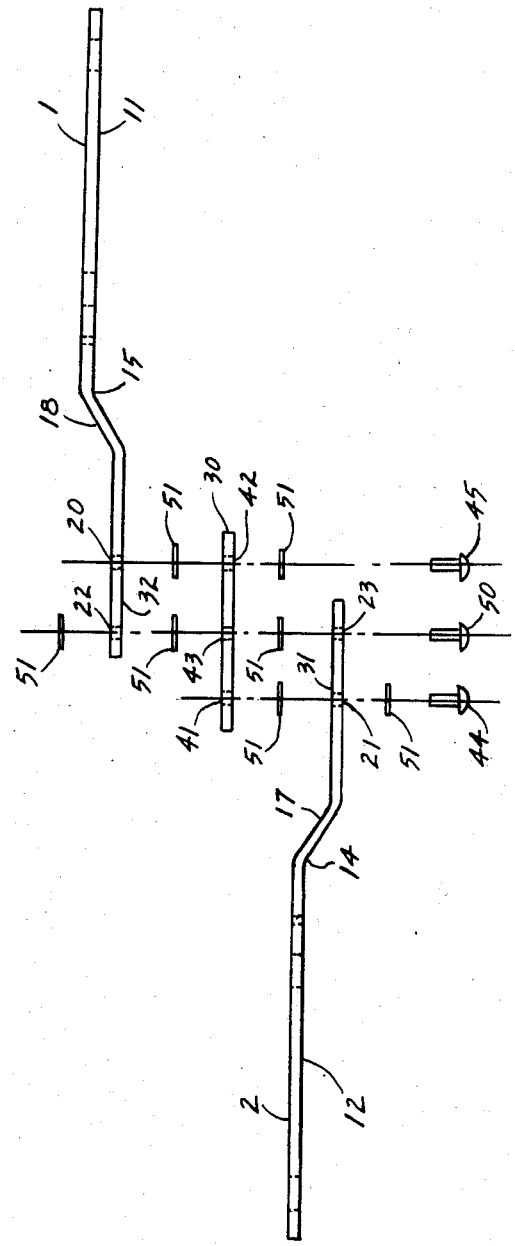

POLYCENTRIC VARIABLE AXIS HINGE

FIELD OF THE INVENTION

This invention relates to a new improved polycentric variable axis hinge. More particularly, this invention relates to a hinge having improved extension and flexion movement, which is especially useful when incorporated as the pivotal system in the design of orthotic devices. Of special utility is the use of the novel polycentric variable axis hinge in hinged knee-joint supports or more involved functional knee braces.

BACKGROUND AND PRIOR ART

Knee braces are known in the prior art. The movement of the knee joint is limited in certain cases, but in almost every instance the braced knee is permitted some movement. The knee-joint is made up of two condyloid joints and a third joint, partly arthrodial, but not completely, since the articular surfaces are not mutually adapted to each other. The resulting movement is not a simple gliding motion. The principle movements that take place at the knee joint are flexion and extension.

The movements of flexion and extension at this joint differ from those in a typical hinged joint, such as the elbow or hip. The axis around which motion takes place in the knee joint is not fixed, but the axis shifts forward during extension, as the gliding movement is superimposed on the rolling motion and the axis shifts backward during flexion.

Although the knee joint has been described as a hinged joint in the prior literature; it has a more complicated character. The knee joint must be regarded as consisting of three articulations, of two different kinds. The first is a condyloid articulation; in this form of the joint, an ovoid articular surface, or condyle, is received into an elliptical cavity in such a manner as to permit flexion, extension, abduction, adduction, and circumduction, but no axial rotation. The second kind of articulation involved is arthrodial; this is a joint which permits only gliding movement. It is formed by the apposition of plane surfaces, or one slightly concave, the other slightly convex. The amount of motion between these surfaces is limited by the ligaments or osseous processes surrounding the articulation.

When damage or injury occurs to the knee joint some form of suitable bracing is required. Associated with the bracing, in order to permit movement, as flexion and extension of the knee joint, there is a hinged structure pivotal about the knee joint.

Previous known knee braces and protective devices contain simple hinged structures or more recently a biaxial hinge. All of the previously designed hinges attempted to parallel the complex movement of the knee joint. Some knee braces for support and protection of the knee joint incorporate both an inner and an outer bracing structure.

Anderson, U.S. Pat. No. 4,249,524, discloses a true biaxial or double hinged pivotal brace and knee stabilizer. McDavid, U.S. Pat. No. 3,528,412, describes a brace with a fixed single pivot hinge. Rigdon, U.S. Pat. No. 4,219,892, discloses a knee brace having an accordian-folded section filled with fluid and held together with tension straps.

French Patent Application No. 79-10960 discloses a "link" hinge. The intermediate link has a longitudinal slot, the slot allows one of the uprights to move only in the direction of the longitudinal axis. The other end of the link has a fixed pivot to which is connected the other upright or brace extension. Canadian Pat. No. 1,011,204 relates to a knee brace with a dual planer link element between the elongated upper and lower arms of the brace. The arm and connecting link are essentially planer and are limited in pivotal motion to the plane of the link element and the front and back stops of the link element has an upper and lower pivot points spaced apart by a distance range of about $\frac{3}{4}$ of an inch to about 2 inches.

Frank, U.S. Pat. No. 4,340,041, relates to an articulate splint having upper and lower anchor bars connected to a lock plate. The lock plate contains a hinge means. The hinge means in the lock plate has a single pivotal axis. Taylor, U.S. Pat. No. 3,902,482, describes a mechanical joint for orthopedic braces or prosthesis. The joint has an upper and lower portion attached by a link. Each portion has dual bearings which combine to provide a pivotal movement closely simulating the flexing action of a knee.

Meany, U.S. Pat. No. 2,460,895, relates to a joint protector having a longitudinally movable hinged joint; one fixed pivotal end, and one pivotal and longitudinally sliding connection. Goodwin, U.S. Pat. No. 58,403, relates to a surgical splint with a movable hinge having a set-screw moving in a slot and a single fixed pivot. Barry, U.S. Pat. No. 1,374,177, relates to an orthopedic appliance having a free pivotal connection and a means for fixing the connection so as to form a rigid structure. There is no provision for movement.

Rossman, U.S. Pat. No. 3,581,741, relates to a partially leg encircling knee brace with a hinge means on the upper inside body portion which includes a single rivet and a single pivot pin or rivet connecting a bar between the upper hinge and the lower body portion of the brace. Clegg, U.S. Pat. No. 901,592, relates to bracing device with a single pivot in conjunction with slide button in the slot which together allow vertical movement as well as single point pivot. Peckham, U.S. Pat. No. 2,467,907, describes a knee brace having springs pivotally attached top and bottom to two centrally disposed shaped plates on the inside and outside of the knee joint. In effect each pivot point is a rotary pivot at a single point. Peckham, U.S. Pat. No. 3,194,233, relates to a corrective and protective knee brace which has a pair of curved pressure members on opposite sides of the knee joint. The curved pressure members contain hinge joints which are made up of conventional hinge parts.

McClure, U.S. Pat. No. 3,350,719, relates to a knee brace having an upper bar and a lower bar which are pivotally joined with a hinge arrangement. The hinge in McClure is a link bar with an upper pivot pin and a lower pivot pin. The pivot pin provides a double conventional pivoting hinge joint connecting the upper brace bar and the lower brace bar through the link bar.

Each of the prior art hinges associated with the knee braces or protective devices, includes a simple pivoting hinge, either alone as a single pivot point or a pair of single pivot points spaced apart or in close proximity. All of the prior braces attempt to provide a hinge device to emulate and move parallel to the complex movement of the knee joint. Some braces are in place when the leg is extended, but fail to accurately follow the knee motion when flexed.

SUMMARY OF THE INVENTION

A principle object of this invention is to provide a new variable axis pivotal joint system for use in knee braces, protective devices and other similar orthotic devices so constructed to accurately follow the complex movement of the knee joint and similar human and animal body joints.

Another object of the invention is to provide a polycentric variable axis pivotal joint system which can be adjusted to control extension and flexion to accommodate symptomatic or rehabilitative instabilities.

A further object is the provision of a polycentric variable axis pivotal joint system which is constructed to allow only pivotal movement and not lateral movement of the hinged body joint.

Other important objects and purposes of the instant invention will be disclosed and apparent in the following detailed description and the specification and the drawings to which reference is made.

BRIEF DESCRIPTION OF THE DRAWINGS

FIG. 1 is a planer view of the variable axis pivotal hinge system in the extended position.

FIG. 2 is a planer view of the variable axis pivotal hinge system in the flexion position.

FIG. 3 is a side view showing the construction of the variable axis pivotal hinge system of FIG. 1.

FIG. 4 is an exploded side view of the variable axis pivotal hinge showing the elements of construction and their assembly.

DESCRIPTION OF THE INVENTION

With reference to the drawings, FIGS. 1–4, the polycentric variable axis pivotal hinge of the present invention comprises an upper extension 1 and a lower extension 2 secured together by the variable axis hinge. Each extension has a complementary angular offset to keep the extensions in parallel, offset planes and yet incorporate the hinge.

As best illustrated in FIG. 4, it will be seen that the upper extension 1 is angularly offset at its upper portion 11 and maintains this offset configuration down to a point just before the hinge as indicated at 15. A similar complementary configuration is indicated for the lower extension 2 at 12 and 14. Angular interconnecting means 17 and 18 displace the hinge outward from the body joint and each secures a portion of the hinge at 20 and 21.

The polycentric variable axis hinge is made up of a central member 30, which is substantially a flat oval or semicircular or elliptical flat disk-like plate, having an inside surface and an outside surface, and an upper end and a lower end. Said central member is interiorly disposed in an overlying relationship with respect to each lower terminal ends 31 and 32 of the upper extension 1 and the lower extension 2, respectively. The central member 30 is provided with three equally spaced openings: two outer openings along the same axis are holes 41 and 42, one on the upper end and one on the lower end, and a central opening 43 which is an elongated slot equally spaced between the outer openings 41 and 42 perpendicular to the axis on which the outer openings lie.

In the terminal ends 31 and 32 of the upper extension 1 and lower extension 2 each are provided with a short horizontal slot, 22 and 23, opening parallel to the central axis of the angle of offset from the main extensions 11 and 12. The offset of the terminal ends is angular to the longitudinal axis of the extension. Also provided is an annular opening in each of the terminal ends 31 and 32 at 20 and 21 spaced from the horizontal slots 22 and 23 and on the same axis as the horizontal slots 22 and 23.

The central member 30 is interiorly interposed between the lower terminal ends 31 and 32, such that an upper pivot rivet-pin 44 can extend through the mating opening 21 in the lower terminal end 31 and through the mating opening 41 in the central member and is terminated on the outside surface of the central member by a terminating means, such rivet-pins. In a similar manner a pivot pin 45 extends through the mating opening 20 in the lower terminal end 32 and through the mating opening 42 in the central member and is terminated on the inside surface of the central member.

The pivot pins 44 and 45 provide a means for pivotally connecting the upper extension 1 and the lower extension 2 to the central member. A guide pin follower 50 extends pivotally and glidably through the slot 23 in the lower terminal end 31 of upper extension 1, through vertical slot 43 in the central member 30 and through slot 22 in the lower terminal end 32 of lower extension 2. The terminal ends 31 and 32 in which the slots 22 and 23 are located are angled toward the full extension configuration. As shown in FIG. 1. At this extended position the guide pin follower is at the top of the slot 43 in the central member. The upper extension 1 and lower extension 2 are longitudinally aligned with each other and with the central member. The top of the vertical slot 43 in the extended position acts as a stop when the guide pin follower 50 engages the top of the slot, in this way further rotation which results in hyperextension is prevented. The pivotal movements of the upper and lower extensions are limited, so that when they have rotated in a longitudinally aligned position simulating the thigh and calf of the leg when they are aligned in standing position. However, pivotal movement of the upper and lower extension 1 and 2 in the opposite direction is limited only by the flexural limits of the knee joint.

By having a common guide pin follower 50 coacting with the central member 30 and interactive pivots at 20 and 21, which also coact with the central member, there is provided in essence a triaxial hinge. Such a triaxial hinge more naturally follows the complex movement of the human knee. The variable axis hinge action provided when the instant hinge is incorporated into a knee brace in which the upper and lower extensions are approximately laterally aligned with the pivotal portions of end of the femur and the end of the tibia, respectively, affords a very accurate approximation of the true knee action. Thus, in this hinge, the upper extension 1 simulates the action of the femur and the lower extension 2 simulates the action of the tibia. The central member 30 spans the joint space and is connected to each extension 1 and 2 by one individual pivot pin each 44 and 45, and one common guide pin follower 50 in order to simulate the complex pivotal hinge action of the knee.

In its operation and movement from extension to flexion the hinge displays a variable axis with continuously changing central pivot point as the guide pin follower 50 moves within the slot 43 in the center member 30. The slot 43 acts as a guide means for receiving and cooperating with the guide pin follower 50. The movement of the hinge defines the extension and flexion of the extensions 1 and 2. Said guide pin follower causes the motion to be transmitted to angular rotation and pivot about each of the extensions 1 and 2. The pivotal action for each extension is centered on the axis of the pivot points 20 and 21. The slot in each angular terminal portion of the extensions permits the angular motion to follow the horizontal movement of the guide pin follower. Each extension moves in a relative angular movement determined by the coaction of the guide pin follower interacting with the slots in the angular terminal portions of the extensions and the guide pin follower moving in the horizontal slot in the central member. In the central member the spatial placement of the pivot points are spaced apart and equidistant from the central vertical slot, which is perpendicular to the longitudinal axis of the pivot points 41 and 42.

Bushing members formed separately from the pivot or pin are used in the hinge to cooperate with the pivot or pin and further assist in the ease of movement of the various members of the instant hinge. Since the movement and relative ease of movement is important for the successful acceptance of the device by potential users. Alternative, to the use of bushings for the pivot pins is the use of washers or gaskets placed between the pivot pin head or terminal portion and the surface immediately registerable with said pivot pin or rivet head or terminal portion. Also bushings or washers maybe placed between registerable surfaces, as between the extension terminal portion and the central member.

A series of spaced holes 61-68 are provided in the central member 30 for insertion or adaption of bumpers or stops or limit the extent of pivot movement. Hence the bumpers or stops are adapted to engage the lower terminal ends 31 and 32 of the upper and lower extensions and prevent the further movement of the extensions. Hyperextension and excessive flexion by the knee is prevented by use of said bumpers or stops placed in holes 61 through 68. The bumpers or stops may be set screws or the like placed in threaded holes. Thus, the hinge imposes no vertical axial restraint unless said bumper or stop is in place. The only other restraint is the guide pin follower 50 within the slot 43 as described above, when the guide pin 50 engages the top extreme of the slot 43. The hinge imposes restraint in compression, and no stress when the knee is flexed.

The present polycentric variable axis hinge is very compact and light in weight. It may be made of a light metal or alloy, or it may be made of a rigid plastic material.

Preferably, the material of construction is stainless steel. The upper and lower extensions may be covered or placed in a soft resilient covering—woven, knitted or one or two way stretch fabric, sponge rubber or similar resilient material sleeves and secured therein by stitching or adhesive or both. These features adapt the hinge to comfort of the user. For certain other uses the extensions may be embedded in plastic or plaster of Paris for fitting to the users leg or the like.

It will be apparent to those skilled in this art that various changes may be made in the invention without departing from the spirit and scope thereof, and therefore the invention is not limited by that which is shown in the drawings and described in the specification, but only as indicated and defined in the appended claims.

What is claimed is:

1. A polycentric variable axis hinge for orthotic devices comprising:
    an upper extension and a lower extension each having lower terminal ends, said terminal ends each having a short horizontal slot and an opening to receive a pivot means and each terminal end angularly disposed with respect to the extensions;
    a center link member interiorly disposed in a partial overlying configuration between said upper extension terminal end and lower extension terminal end having an upper end and a lower end and an inside surface and an outside surface, said center member having three equally spaced openings a vertical slot and two equally distanced holes therefrom in said upper and lower ends;
    said upper extension overlying the outside surface of the center member so that the short horizontal slot in the terminal end cooperates with the vertical slot in the center link member and the opening in the upper extension cooperates with the opening in the terminal of the upper extension accepting a common means for pivotally joining them; said lower extension overlies the inside surface of said center link member in a similar manner with cooperating slots and openings;
    means for pivotally connecting said terminal end of said lower extension to said inside surface through said cooperating openings and said terminal end of said upper extension pivotally connected to said outside surface through said cooperating openings; said slot in the terminal end of said lower extension and the slot in the terminal end of said upper extension slidably and pivotally connected to said slot in said center link member with a common means for slidably coupling therewith.

2. In the device of claim 1 in which the upper extension and lower extension each have an angular offset to keep each extension substantially in the same plane and the hinge offset from the body joint.

3. In the device of claim 1 in which a series of spaced holes are provided in the central link member and stop means are inserted therein to engage the lower terminal ends of the upper and lower extensions to limit the extent of relative pivotal movement therebetween to prevent hyperextension of the joint.

4. In the device as in claim 3 wherein the spaced holes are in the form of threaded holes and in which said stop means is a set screw adapted to be received in said threaded holes.

5. The device of claim 4 including stop means for limiting flexion movement of the hinge in one direction beyond a position assumed when the body joint is substantially straight.

6. A polycentric variable axis hinge having a center link member having a center horizontal slot and two equally spaced openings on either side of said center link member; overlying upper extensions and an overlying lower extension each having a vertical slot and spaced opening; said center link member and the upper and lower extensions share a common pivot point means with each other and the vertical slots and with the interiorly disposed center link member at the horizontal slot; each extension having a vertical slot on the axis with said spaced openings; each spaced opening pivotally connected separately to said equally spaced opening in the center link member whereby the center link member and upper and lower extensions are rotatable about the longitudinal axes and are commonly moveable toward and away from each other.

7. The device of claim 6 wherein said common pivot means is a follower guide pin.

8. The device of claim 6 wherein the center link member has a series of spaced holes, the arrangement being such that when stop means are inserted therein relative pivotal movement of said extensions is restricted.

* * * * *